United States Patent [19]

Castel

[11] Patent Number: 5,413,550

[45] Date of Patent: May 9, 1995

[54] ULTRASOUND THERAPY SYSTEM WITH AUTOMATIC DOSE CONTROL

[75] Inventor: John C. Castel, Topeka, Kans.

[73] Assignee: PTI, Inc., Topeka, Kans.

[21] Appl. No.: 95,102

[22] Filed: Jul. 21, 1993

[51] Int. Cl.$^6$ .............................................. A61H 1/00
[52] U.S. Cl. ............................................ 601/2; 601/3; 607/97
[58] Field of Search ......................................... 601/2–4; 607/97; 604/22

[56] References Cited

U.S. PATENT DOCUMENTS

| | | | |
|---|---|---|---|
| 4,368,410 | 1/1983 | Hance et al. | 601/2 |
| 4,614,178 | 9/1986 | Harlt et al. | 601/2 |
| 4,763,663 | 8/1988 | Uphold et al. | 128/715 |
| 4,791,915 | 12/1988 | Barsotti et al. | 601/2 |
| 5,086,788 | 2/1992 | Castel et al. | |
| 5,230,334 | 7/1993 | Klopotek | 607/97 |

OTHER PUBLICATIONS

Greenwald et al., "A Computer Controlled System for Ultrasonic Hyperthermia Treatment", Conference: Eighth Annual Northeast Bioengineering Conference, Cambridge Mass. 27–28 Mar. 1980 pp. 129–132.
Castel, J. C., *Therapeutic Ultrasound*, Reprinted From "Rehab and Therapy Products Review", Jan./Feb. 1993, pp. 22–31 with reference List.

*Primary Examiner*—Ruth S. Smith
*Attorney, Agent, or Firm*—Litman, McMahon & Brown

[57] ABSTRACT

An ultrasound therapy system with automatic dose control includes an ultrasound transducer, an ultrasound generator controllable in frequency and power output connected to the transducer, a system controller interfaced to the generator, input switches interfaced to the controller to enable the input of selected ultrasound treatment parameters, and a display interfaced to the controller. The controller is programmed to calculate an ultrasound treatment dosage in terms of frequency, ultrasound intensity, and treatment time from the entered treatment parameters. Once treatment is started, the controller tracks the accumulated dosage applied to the tissue. The clinician can vary the intensity or treatment time, and the controller will recalculate the other factor for the remaining portion of the unapplied treatment dosage.

16 Claims, 3 Drawing Sheets

ULTRASOUND THERAPY SYSTEM WITH AUTOMATIC DOSE CONTROL

BACKGROUND OF THE INVENTION

Ultrasound has been used as a therapeutic technique in physical medicine for over forty years. By 1955, the Council on Physical Medicine and Rehabilitation of the American Medical Association recommended the technique as an adjunctive therapy for the treatment of pain, soft tissue injury, and joint dysfunction including osteoarthritis, periarthritis, bursitis, tenosynovitis, and a variety of musculoskeletal syndromes. Other applications such as acceleration of wound healing, phonophoresis of topical drugs, treatment of scar tissue, and treatment of sports injuries have been reported.

Ultrasonic therapy relies on mechanical vibration of tissue to cause thermal and nonthermal effects, using the conventional therapeutic frequency of 1 Mhz (megahertz) or the newer 3 Mhz frequency. Basically, the electrical output from the ultrasonic generator is converted into mechanical vibration through a transducer made generally of a crystalline material, such as lead zirconate titanate (PZT) or other synthetic or natural crystals. The mechanical vibration produces an acoustic wave which travels through the tissue and is absorbed in the process. The rate of absorption and, thus, the thermal effect is based on the tissue type encountered, the frequency of the ultrasound beam, and the intensity of the ultrasonic output. The energy is transferred from the transducer to the patient's tissue using a coupling medium or couplant, such as ultrasonic gel, lotion, hydrogel, or water. Output may be continuous wave or pulsed depending on the therapeutic indication. Output intensities of 0.1–3.0 W/cm$^2$ (watts per square centimeter) are typically applied for therapeutic purposes in pulsed or continuous modes with ultrasound therapy.

Power output of an ultrasonic transducer may be indicated in watts as the total power emanating from the transducer or as intensity in W/cm$^2$ which is the total acoustic power output divided by the effective radiating area or surface (ERA) of the transducer. Intensity is commonly used for therapeutic ultrasound applications. Continuous wave ultrasound output may also be measured in energy units of joules (watt-seconds) which is the amount of total delivered acoustic power applied to the tissue over the total treatment time. Continuous wave ultrasound is generally used for thermal applications.

Pulsed output is also referred to as amplitude modulated waveform operation. This means that the output turns on and off in short periodic intervals. This reduces the average power delivered to the patient, as compared to continuous output. Output power is displayed as the average power during the pulse of ultrasonic energy. In order to calculate the average power over time, the indicated power output is multiplied by a duty factor, which is defined as the on-time per period divided by the total time of the period, that is, duty factor=-(time$_{on}$)/(time$_{on}$+time$_{off}$). Pulsed outputs are generally used in pain control and tissue healing applications at non-thermal levels. Pulse durations and duty factors should be selected based on clinically tested parameters. Ultrasonic therapy systems should provide a full range of pulsed modes, allowing the clinician to treat acute as well as chronic injury.

In order to accurately portray the output characteristics of ultrasonic therapy transducers, an evaluation of the radiating surface must be made. This can be done using sophisticated testing systems which scan each portion of the transducer with an underwater microphone known as an acoustic hydrophone. Evaluation of the radiating surface of most transducers demonstrates that in the near field (generally within 10–30 cm of the sound head surface), significant irregularities in output intensity exist. These range from little or no intensity to very high peak intensities.

The effective radiating area (ERA) of an ultrasound transducer is determined by scanning the transducer at a distance of 5 mm (millimeters) from the radiating surface and recording all areas in excess of 5 per cent of the maximum power output found at any location on the surface of the transducer. The ERA is always smaller than the actual transducer surface; thus, the apparent size of the transducer is not indicative of the effective radiating surface. For this reason, individual scans of each transducer should be performed to ensure proper calibration of intensity in W/cm$^2$ of ultrasonic output. A common mistake is to assume that the entire surface of an ultrasound transducer radiates ultrasound output. This is generally not true, particular with larger transducers, such as 10 cm$^2$. There is no point in having a large transducer with a small effective radiating surface because such an arrangement mechanically limits the coupling in smaller areas. The transducer ERA should match the physical transducer head size as closely as possible for ease of application to various body surfaces in order to maintain the most effective coupling.

The major measure of beam homogeneity of an ultrasonic transducer is the beam nonuniformity ratio (BNR). Beams from practical ultrasound transducers are not homogeneous in intensity across their wavefronts. The BNR is the ratio of the highest intensity found in the field to the average intensity, as indicated on the output display of the generator. If, for example, the BNR of a transducer is 6:1, as is typical for many ultrasonic therapy transducers, and the intensity is set at 1.5 W/cm$^2$, intensities in the order of 9.0 W/cm$^2$ would be present in the field. The high peak intensities with high BNR's are responsible for the discomfort or periosteal pain often associated with ultrasound treatment.

The higher the BNR, the more important it is to move the transducer faster during treatment to avoid hot spots and areas of tissue damage or cavitation, which refers to microbubble implosions causing small vessel and cell membrane damage. Application technique is, thus, BNR dependent. The allowable intensity of the ultrasound beam should be the lower of patient tolerance to the beam intensity or the transient cavitation threshold of 8 W/cm$^2$, which is calculated by multiplying the BNR by the output intensity. The lower the BNR, that is, the more even the spacial intensity of the beam, the slower the operator may apply the ultrasound to the treatment area without fear of periosteal burning or transient cavitation). Low BNR's provide highly uniform ultrasonic therapy fields, allowing rapid bulk heating, since the clinician is able to move slowly in the treatment area with a homogeneous beam. Accurate measurement of BNR also allows the clinician to select transducers which ensure consistent, uniform beam characteristics.

Absorption characteristics of ultrasound are unique in that the absorption coefficients for many tissues vary linearly with frequency over the range of 1.0 to 5.0

MHz. For this reason, transducers operating at both 1 and 3 MHz ultrasonic frequencies should be available to provide the clinician control the depth of beam and biological effects. Ultrasound energy at 1 MHz has a half value layer (50 per cent energy absorption layer) of 3.0 cm in muscle, whereas 3 MHz has a half value layer of 1.0 cm in muscle. The 3 MHz frequency is selected where the effect is required superficially. This would include reduction of edema in recent injuries and treatment of skin abrasions, bruising, epicondylitis, arthritis of small joints, scar tissue, periostitis, ulcers, and pressure sores. Acute injury responds well to 3 MHz ultrasound treatment, and there is a good analgesic effect. The lower frequency of 1 MHz common to most ultrasonic therapy generators is used to treat more deeply seated lesions where fibrotic or sclerotic conditions exist, widespread contractures in tendon and muscle, and large joints affected by osteoarthritis.

The biological effects of ultrasound may be categorized according to two major areas: thermal effects and nonthermal effects, including acoustic streaming, cavitation, and other mechanical effects.

In local regions of tissue subjected to an ultrasonic plane travelling wave, heat is produced at a rate per unit volume proportional to the level of intensity and the absorption coefficient of the tissue. Under stable conditions, temperature increases at a constant rate, provided the treatment area is limited to an area of approximately twice the ERA of the transducer. Treating too large of an area at a time will result in cooling effects by the normal blood flow, and an inadequate tissue temperature increase will result. Surprisingly, many therapeutic ultrasound treatments given every day in the clinic do not result in temperature increases of noteworthy value, although the clinician's intent was to provide thermal effects. This is due in part to the uneven distribution of ultrasound across the transducer surface (high BNR), the treatment of too large of an area for too short of a time, and the lack of consideration of tissue target location and coupling media.

Tissues with high collagen content most strongly absorb ultrasonic energy at the frequencies commonly used therapeutically. Most soft tissues have similar absorption coefficients. As previously described, beam penetration is a function of frequency. Thus, if one wishes deep heating, the use of 1 MHz ultrasound is indicated, as compared to surface where 3 MHz would be used.

The capability of obtaining reliable temperature increases in the tissue is the key to achieving therapeutic effects. Alterations in cell membrane diffusion, extensibility of collagen, and catalytic reactions times are specifically temperature dependent. In general, the application of therapeutic ultrasound is used to produce heating effects ranging from mild (1° C. tissue temperature increase), moderate (2° C.), or vigorous (4° C.). The higher temperature increases are useful in the treatment of chronic connective tissue and joint diseases such as contracture, chronic scars, and osteoarthritis, whereas the lower temperature increases are used in the treatment of subacute injury and to accelerate tissue repair. It has been noted that thermal levels of ultrasound induce local release of histamine, further increasing blood flow and local microcirculation. Other researchers have demonstrated that the selective heating of nerve tissue may produce temporary conduction blocks in nerve action potential propagation. This may be a factor in blocking pain with ultrasonic therapy applied at thermal levels.

Regarding nonthermal effects, acoustic streaming is an effect produced by the ultrasonic beam within the tissue which occurs primarily at the cell membrane interface. Streaming is the unidirectional movement of tissue components exposed to the ultrasonic field. This effect has been observed by many investigators, and is thought to be responsible for affecting cellular diffusion rates, membrane permeability, and accelerated synthesis of collagen. It should be noted that these stimulatory effects generally occur at low intensity, pulsed modes of 3 MHz ultrasound and are not evident at higher intensities and different frequencies. The primary effects on collagen synthesis and healing rates appear to occur at an early stage of the regeneration process during active growth and proliferation. Reactions limited by diffusion rates including the re-absorption of exudates may be accelerated by streaming effects. These movements also contain enough energy to enhance the making or breaking of weak secondary hydrogen bonds, thus accelerating enzymatic reactions.

It has also been found that platelets exposed to ultrasonic fields release serotonin. This may help to explain pain reduction effects, since serotonin is an important neurotransmitter involved in the release of endogenous opiates, such as enkephalins and dynorphins. Increased phagocytic activity and bactericidal capacity have also been observed with five minute ultrasonic energy exposures at therapeutic levels of insonation.

Cavitation is a condition where gas bubbles form within the tissues as a result of ultrasonic radiation. These bubbles oscillate within the ultrasound field at the ultrasonic frequency. Stable bubble formation in vivo has been observed using acoustic imaging techniques at intensities in the therapeutic range at intermuscular interfaces. Low level cavitation and mechanical micromassage at the cellular level is thought to be responsible for cellular stimulation, edema reduction in post traumatic injury, as well as the stimulation of mechanoreceptors and the autonomic nervous system. Sympathetic, parasympathetic, and sensory stimulation by ultrasound in pulsed modes may account for the pain relieving effects often associated with ultrasonic therapy. Some researchers have demonstrated increased nerve conduction velocity following insonation of nerve tissues. It is apparent from many clinical observations that ultrasound produces significant analgesic effects in a large percentage of patients on account of both neurologic stimulation and the anti-inflammatory effects of ultrasound on tissues.

As described above, ultrasound therapy has measurable and otherwise verifiable thermal and nonthermal effects on various types of tissues depending on various parameters of the applied acoustic energy and manner of application to tissues. Thus, control of the parameters of therapeutic ultrasound would provide a clinician with the capability of treating a great variety of ailments with predictable results. However, the great majority of ultrasound treatments are applied with fixed parameters, usually 1 MHz at 1.5 W/cm$^2$ for five minutes with a relatively high BNR transducer, regardless of the area or depth of intended tissue treatment. Although some nonthermal benefits may be derived from such an approach, the thermal benefits usually intended are seldom realized from such an imprecise application of ultrasound.

While clinicians, such as osteopaths, chiropractors, and physical therapists, and others who employ therapeutic ultrasound are usually knowledgeable in their respective areas of specialty, they are usually not trained to make the necessary adjustments to therapeutic ultrasound instruments which would enable the wide variety of treatments of which the application of ultrasound is capable. Therefore, an approach which would facilitate the control of ultrasound transducer parameters in relation to the type and location of tissue to be treated and the desired effect on the treated tissue would be of considerable benefit to the patient receiving the treatment.

SUMMARY OF THE INVENTION

The present invention provides apparatus and methods for applying ultrasound to the treatment of tissues which facilitates the insonation of tissues with a precise "dose" of ultrasound energy which is calculated on the basis of treatment parameters input into the apparatus. In general the apparatus includes an ultrasonic transducer, an ultrasound generator controllable in frequency and power output connected to the transducer, an ultrasound controller including a microprocessor interfaced to the ultrasound generator, ultrasound parameter input switches interfaced to the controller, and a display interfaced to the controller. The transducer preferably has a low beam non-uniformity ratio (BNR), and the apparatus preferably includes multiple transducers having heads with different effective radiating areas to facilitate treatment of different sized areas of tissue. The ultrasound generator includes a radio frequency oscillator operable at one and three megahertz along with a radio frequency amplifier with a controllable power output.

The controller is programmed to calculate a treatment dose of ultrasound energy in terms of treatment frequency, output intensity ($W/cm^2$), and treatment time based on the clinician's selection of a number of treatment parameters. The treatment parameters include primarily the depth of tissue to be treated, the desired tissue temperature rise as a result of treatment, the area of tissue to be treated, and a selection of an ultrasound couplant. The treatment parameters may also include a selection of tissue type and duty factor of the ultrasound output signal. Preferably, the control program reverts to default treatment parameters if no treatment parameters are entered.

The selected tissue depth determines the frequency of the ultrasound output signal. A three megahertz signal is absorbed within a relatively shallow depth of tissue, depending on the character of the tissue. A one megahertz signal has less absorption in shallow layers and therefore penetrates to greater depths in comparison to a three megahertz signal.

The output intensity of the transducer for a given treatment is determined by the desired temperature rise of the target tissue and the type of the target tissue, the ultrasonic transmission characteristics of the coupling medium employed and of tissue intervening between the transducer and the target tissue, and the area of application of the target tissue. Thermal ultrasound treatments are characterized as mild, moderate, and vigorous, corresponding to tissue temperature increases respectively of one, two, and four degrees Celsius. The ultrasonic transmissivity of coupling media or couplants range from nearly 100% for water and 96% for aqueous gel to 68% for hydrogel. The control program of the present invention provides for the selection of one of a number of common ultrasonic couplants. Ultrasound energy absorption in the selected couplant is factored into the determination of the amount of ultrasound energy which can be transferred to the target tissue. Various types of tissues have different ultrasound absorption characteristics, ranging from low absorption in fat, moderate absorption in muscles, higher absorption in connective tissue such as tendons and ligaments, and the highest absorption in bone tissue.

The ultrasound power output of the transducer is applied over its effective radiating area (ERA). The controller is programmed to break down a relatively large treatment area entered into a number of treatment segments consisting of a few multiples of the ERA of the transducer employed. The control program tracks the completion of each treatment segment and alerts the clinician as each segment is complete. This avoids spreading the available ultrasound energy over an area too large which would otherwise result in no effective treatment being applied. The duty factor of the output signal is a measure of the ultrasound power applied over time by a pulsed ultrasound signal and is defined as the ratio of on-time to the total period of a pulsed ultrasound signal.

After the treatment parameters have been entered and the treatment dosage has been calculated, the clinician may initiate the treatment of a first segment. In general, it is desirable to apply the maximum amount of ultrasound intensity for the shortest period of time consistent with the avoidance of tissue damage and with the comfort of the patient, to avoid cooling effects caused by increased bloodflow triggered by the increase in temperature of the treated tissue. A low BNR transducer allows the application of a high average intensity over the ERA of the transducer without the problems associated with high peaks of energy from the transducer. The control program limits the output intensity to below the transient cavitation threshold of 8 $W/cm^2$. An increase in output intensity causes a decrease in the remaining treatment time to maintain the same cumulative dose of ultrasonic energy.

In practice, the clinician increases the output intensity until the patient experiences discomfort, at which point the intensity is decreased in increments. The control program tracks the cumulative energy applied and recalculates the remaining treatment time based on the new intensity level and the remaining treatment dosage to be applied. Alternatively, the clinician can vary the treatment time whereby the control program recalculates the output intensity for the remaining dosage. When treatment of the area segment is complete, the control program alerts the clinician to move to the next segment, and the process is repeated.

OBJECTS AND ADVANTAGES OF THE INVENTION

The principal objects of the present invention are: to provide an improved therapeutic ultrasound system; to provide such a system which more effectively exploits the therapeutic capabilities of ultrasound treatment than existing systems; to provide such a system which facilitates the precise use of ultrasound therapy by clinicians for more beneficial treatment of patients; to provide such a system in which an ultrasound transducer is controlled by a computer which is programmed to calculate a treatment dosage of ultrasound energy in terms of a calculated ultrasound output intensity over a calculated treatment time based on treatment parameters entered by the clinician; to provide such a system in which the treatment dosage is calculated based on the depth of tissue to be treated, the desired tissue temperature rise in response to the treatment, the area of tissue to receive ultrasound treatment, the ultrasound coupling medium, the type of tissue to be treated, and the duty factor of the ultrasound signal; to provide such a system which tracks the cumulative dosage applied and which allows the clinician to vary either the intensity or treatment time and recalculates the other factor for the remaining portion of the treatment dosage still to be applied; to provide such a system which prevents adjustments beyond a range which might cause tissue injury from the ultrasound energy; and to provide such a therapeutic ultrasound system which is economical to manufacture, which is precise and convenient in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification, include exemplary embodiments of the present invention, and illustrate various objects and features thereof.

DETAILED DESCRIPTION OF THE INVENTION

Figure 1:
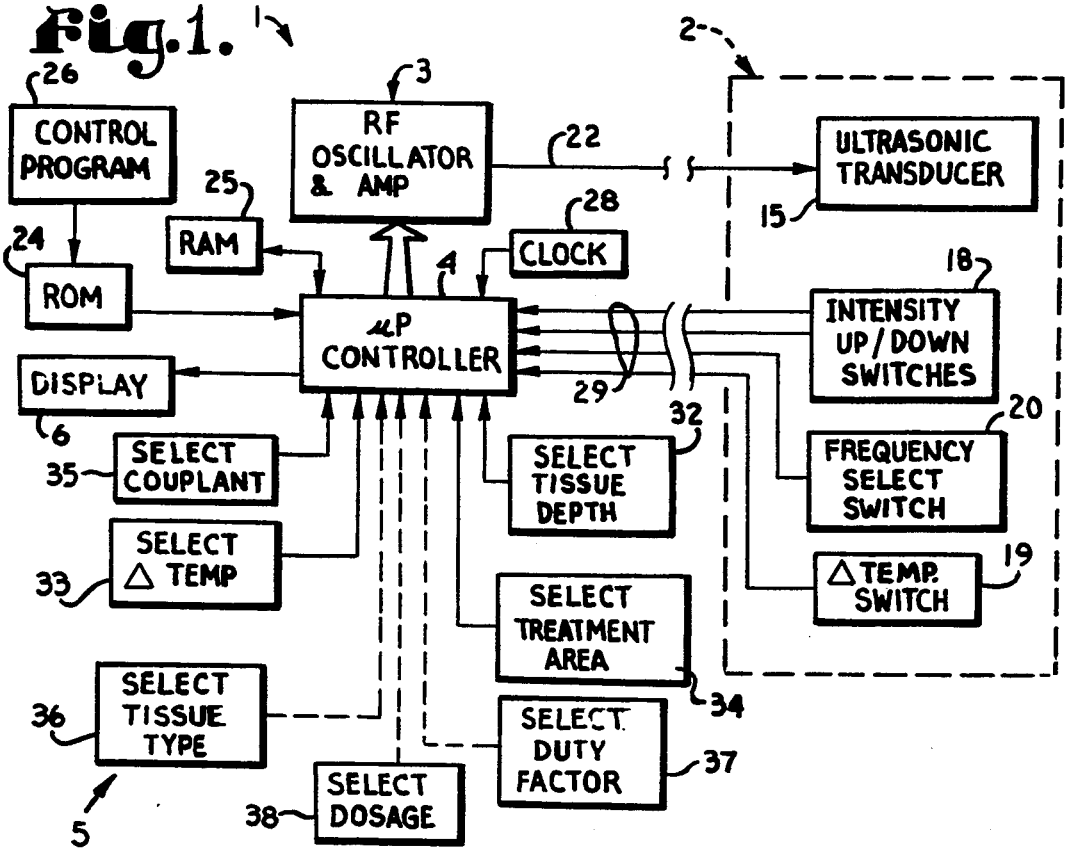
FIG. 1 is a block diagram illustrating the principal components of a therapeutic ultrasound system which embodies the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a therapeutic ultrasound system which embodies the present invention. The system 1 generally includes an ultrasound transducer unit 2, ultrasound generator circuitry 3, a system controller 4 (FIG. 1), a plurality of treatment parameter input switches 5, and a system display 6. In general, the system 1 calculates a treatment dosage of ultrasound energy to be applied by the transducer unit 2 based on treatment parameters entered by operation of the input switches 5 and maintains the calculated output intensity of the unit 2 over the calculated treatment time to achieve the calculated treatment dosage.

Figure 2:
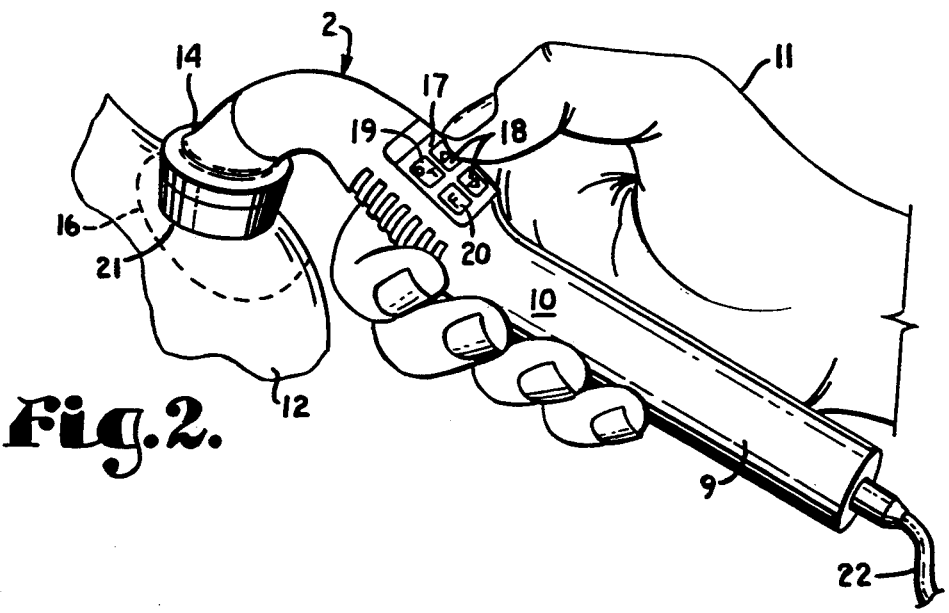
FIG. 2 is a fragmentary perspective view of an ultrasound transducer unit suitable for use in the system of the present invention.

The transducer unit 2 (FIG. 2) includes a housing 9 forming a handle 10 for manipulation of the unit 2 by a clinician 11 to apply ultrasound energy to the tissue 12 of a patient. A distal end of the housing 9 supports a transducer head 14 having an ultrasonic transducer element 15 mounted therein. Excitation of the transducer element 15 by a radio frequency signal from the generator 3 causes ultrasonic vibration of the element 15 which is ultrasonically coupled to the tissue 12 by an ultrasonic coupling medium or couplant 16. The illustrated unit 2 has a switch panel 17 thereon with intensity up/down switches 18, a delta-temperature switch 19, and a frequency select switch 20. Further details of a representative type of ultrasonic transducer unit suitable for use in the system 1 of the present invention can be found in U.S. Pat. No. 5,086,788, issued Feb. 11, 1992, which is incorporated herein by reference.

The transducer element 15 and a radiating membrane 21 of the transducer head 14 are mutually configured to result in a low beam non-uniformity ratio (BNR) which is not greater than 4:1 and which is preferably on the order of 2:1. The use of a low BNR transducer unit allows the application of a high average intensity without exceeding the transient cavitation threshold or causing excessive patient discomfort which can result from intensity peaks present in the ultrasound beam of an transducer with a higher BNR.

The ultrasound generator circuitry 3 includes a radio frequency (RF) oscillator controllable in frequency and a power amplifier controllable in power output. Preferably, the oscillator is controllable to select either one megahertz for relatively deep tissue treatment or three megahertz for shallower treatment. The amplifier portion of the generator 3 may be controllable for output power through a continuous range or may be controllable in convenient power output increments. In other respects, the components of the ultrasound generator circuitry are essentially conventional in construction and operation. An ultrasonic drive signal is communicated from the generator circuitry 3 to the transducer unit 2 over a drive cable or drive portion of a cable 22.

The system controller 4 is essentially a microprocessor with suitable support circuitry, such as interface circuitry (not shown), read-only memory (ROM) 24, read/write memory (RAM) 25, and the like. An exemplary microprocessor for use in the system 1 is the Intel 8088, although a number of other microprocessors and microcontrollers could alternatively be employed. A control program 26 is stored in the ROM 24 and includes routines for the overall control of the system 1, including diagnostic routines, as well as an ultrasound treatment control program 27 (FIG. 5) which controls operation of the transducer 15 during ultrasound treatments. The microprocessor 4 also includes a clock circuit 28 which controls timing functions of the microprocessor 4.

The transducer housing mounted switches 18–20 are interfaced to the controller 4, and conductors 29 therefor are routed within the structure of the drive cable 22. The display 6 is preferably mounted on a console (not shown) having other portions of the system 1, other than the transducer unit 2, mounted therein. The treatment parameter input switches 5 are also mounted on such a console and are interfaced to the controller 4. The primary treatment parameter input switches 5 include a tissue depth selection switch 32, a tissue temperature increase selection or delta-temperature switch 33, a treatment area selection switch 34, and a couplant selection switch 35. Secondary treatment parameter input switches include a tissue type selection switch 36 and a duty factor selection switch 37. The secondary parameter input switches 36 and 37 are preferably included in the system 1 and increase the flexibility thereof, but are not essential to its basic operation. Alternative to entering individual treatment parameters, a clinician may simply select a desired ultrasound dosage by operation of a dosage selection switch 38. The switches 32–38 may be operated in cooperation with the display 6 to cycle through a plurality of selections for each treatment parameter.

The present invention approaches the ultrasonic treatment of tissue in terms of a "dosage" of ultrasonic energy applied to the target tissue. The treatment dosage has energy density units of joules per square centimeter ($J/cm^2$) which is dimensionally equivalent to watt-seconds per square centimeter ($W-sec/cm^2$). Ultrasonic output intensity is measured in watts per square centimeter ($W/cm^2$); thus, ultrasound treatment dosage can also be considered to be the application of ultrasound energy to tissue at a certain intensity ($W/cm^2$) for a required treatment time (sec). Ultrasound intensity and treatment time are referred to herein as dosage factors since the treatment dosage is the mathematical product of intensity and treatment time. In ultrasound treatments intended to cause thermal effects in the target tissue, the dosage is calculated to cause a selected temperature rise in the selected tissue, given the other treatment parameters which affect the transfer of ultrasonic energy from the transducer to the target tissue.

In general, the system 1, and the treatment control routine 27 in particular, enables the entry of various treatment parameters, calculates the frequency of operation and treatment dosage based on the entered parameters, and sets the oscillator and amplifier portions of the ultrasound generator 3 to output an ultrasound drive signal of the calculated frequency and power to the transducer 15 having a given effective radiating area (ERA) and sets a timer control 40 (FIG. 3) to the time required at the set power level to output the calculated dosage from the transducer 15 of a given ERA. Once treatment is started, the system 1 tracks the cumulative dosage applied. Either the output intensity or the treatment time can be varied during treatment, and the routine 27 will recalculate the other dosage factor for the remaining portion of the originally calculated dosage to compensate for the variation in the first dosage factor.

Figure 5:
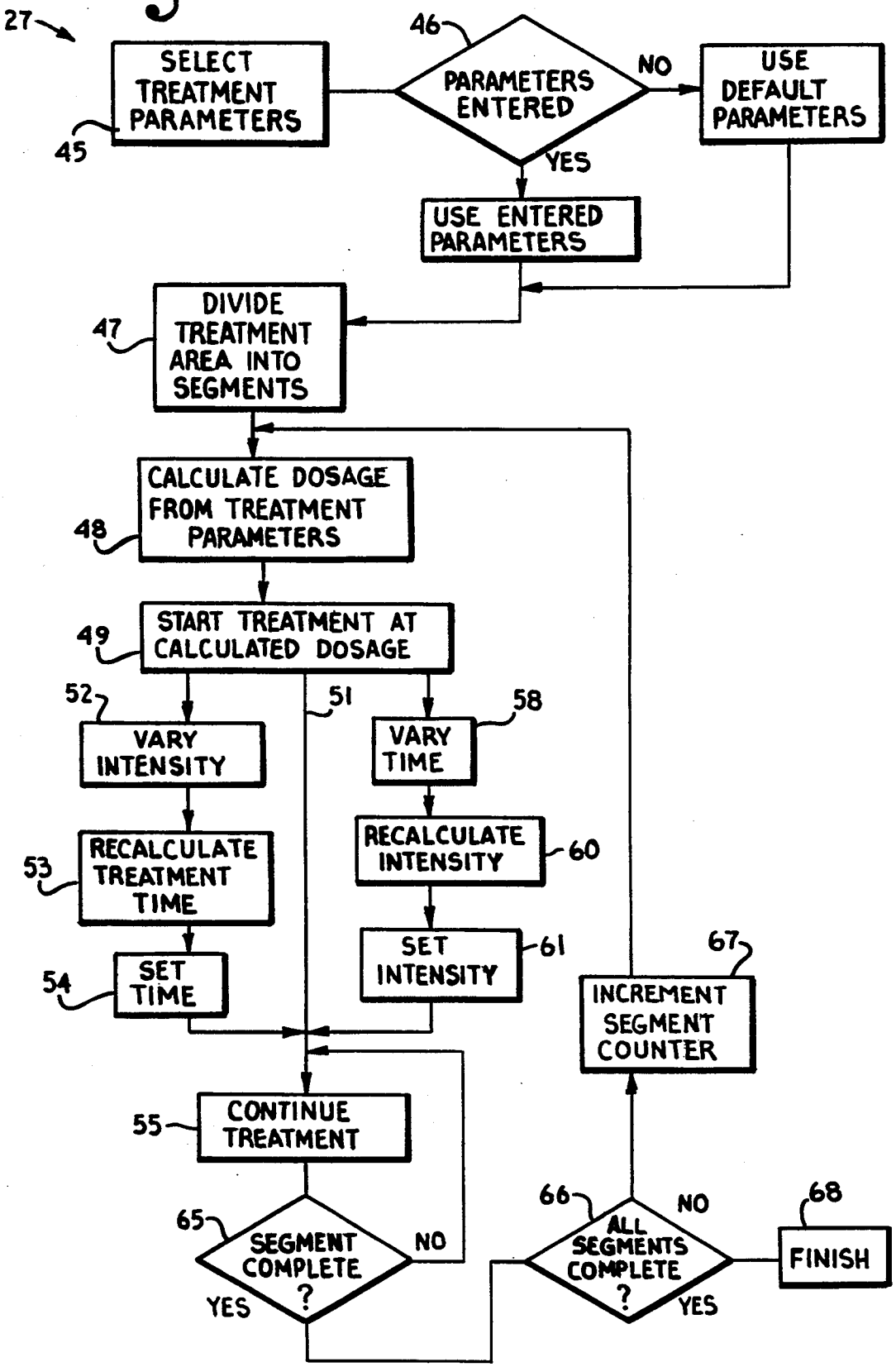
FIG. 5 is a flow diagram of the main components of the control program of the therapeutic ultrasound system of the present invention.

Referring to FIG. 5, the treatment control routine 27 is diagrammatically illustrated. At 45, the treatment parameters are entered by operation of the parameter selection switches 32–37. At 46, the routine 27 checks to see if treatment parameters have been entered. If any of the treatment parameters have not been entered, the routine 27 uses corresponding default parameters. The default parameters may, for example, be a tissue temperature rise of 4° C., deep tissue (implying 1 MHz operation), aqueous gel as a couplant, and a treatment area of 2 ERA's. The system 1 can alternatively be set up to use other default parameters.

The ultrasound energy from the transducer 15 must be applied to a definite area of tissue 12 in order to cause the desired tissue temperature rise. The entered treatment area is divided into treatment area segments at 47. To the extent possible, the treatment area is divided into equal area segments of several ERA's each for the transducer unit 2 employed. Thereafter, the dosage is calculated individually for each segment or the total dosage for the entire treatment area can be calculated and divided into segment dosages proportional to the area of the segments. At 49, the treatment is started whereby the transducer element 15 is energized at the selected frequency and at the calculated dosage or energy density.

During treatment, time is measured by the timer control function 40 which is updated by a time signal or clock interrupt from the system clock 28. The clinician can apply the treatment at the calculated intensity for the calculated treatment time, as indicated by the default line 51. However, because heating of tissue will eventually trigger increased bloodflow in the treated area which will cause an effective cooldown, it is advantageous to increase the output intensity to the tolerance level of the patient and conduct the treatment in a minimum amount of time.

A variation in the output intensity at 52, by operation of the switches 18, causes the routine 27 to recalculate the treatment time at 53 for the remaining portion of the unapplied dosage initially calculated. The recalculated time is set into the timer control function 40 of the routine 27 at 54, and treatment continues at 55. Alternatively, the clinician can vary the treatment time at 58 by operation of a timer control 59 (FIG. 4), in which case, the routine 27 recalculates the output intensity at 60 for the unapplied dosage and sets the recalculated intensity at 61 to an intensity control function 62 of the routine 27 (FIG. 4) The intensity control function 62 is used by the routine 27 to physically adjust the power output of the amplifier section of the ultrasound generator 3. Thereafter, treatment continues at 55. Either the intensity or treatment time can be varied at any time prior to expiration of the treatment time. The routine 27 checks increases in intensity to prevent the peaks of output intensity, as determined from the BNR of the transducer unit 2 employed, from being increase beyond the transient cavitation potential of 8 $W/cm^2$.

Periodically, the routine 27 polls the timer control 40 at 65 to determine if the treatment is complete for the current area segment. If not, treatment continues at 55. If treatment of the current segment is complete, the routine 27 checks a segment counter at 66 to determine if all segments have been treated. If not, the segment counter is incremented at 67, and the dosage for the next area segment is calculated at 48. Alternatively, if the segments are of equal area, control may be returned to the start treatment block 49. When all segments have been treated, the routine 27 enters a wait mode at "finish" 68, at which calculations and control for a new treatment can be initiated.

Figure 3:
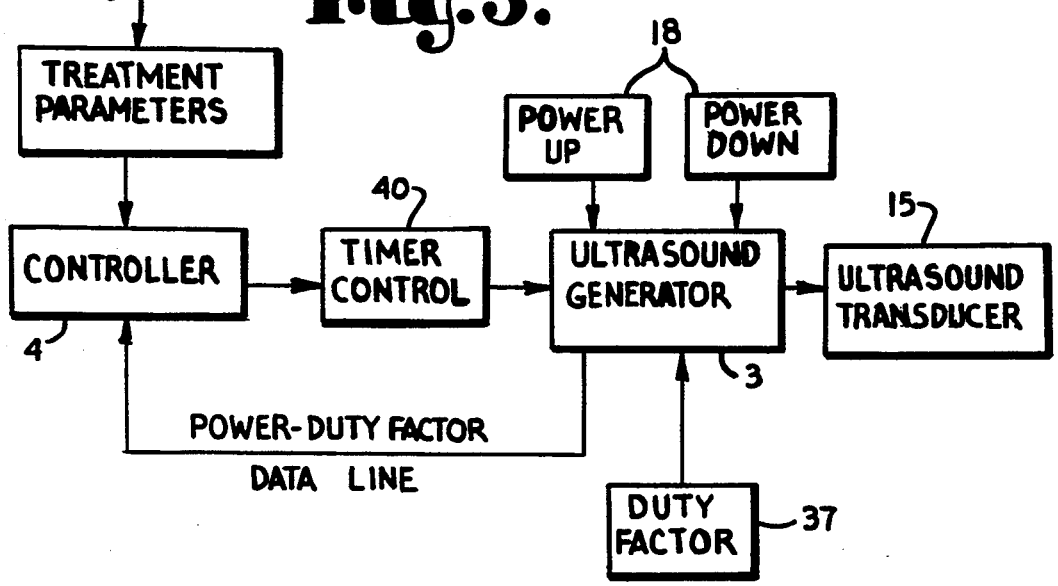
FIG. 3 is a conceptual block diagram of the ultrasound control system of the present invention in which the ultrasound intensity of a calculated treatment dosage is varied.
Figure 4:
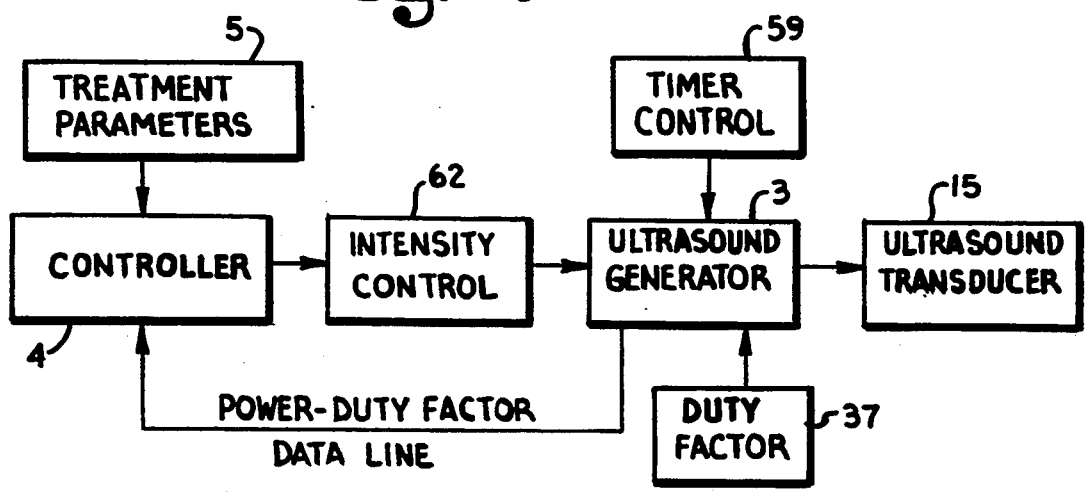
FIG. 4 is a conceptual block diagram of the ultrasound control system of the present invention in which the treatment time of a calculated dosage is varied.

The treatment control routine 27 is an exemplary embodiment of the ultrasound therapy method of the present invention. Variations in the routine 27 are foreseen and are intended to be encompassed within the spirit of the invention. FIGS. 3 and 4 diagrammatically illustrate the control functions of the system 1 based on variation of the ultrasound output intensity in FIG. 3 and variation of the treatment time in FIG. 4.

The routine 27 has been described in terms of calculation of a treatment dosage based on a desired temperature increase in the treated tissue. For non-thermal treatments and for repetitions of treatment of a particular tissue of a patient, it might be more convenient for the clinician to enter a treatment dosage directly, by use of the dosage selection switch 38. When the dosage is entered directly, the routine 27 calculates and maintains a default ultrasound intensity and treatment time or compensates for manual variations in the intensity or treatment time.

It is to be understood that while certain forms of the present invention have been illustrated and described herein, it is not to be limited to the specific forms or arrangement of parts described and shown.

What is claimed and desired to be secured by Letters Patent is as follows:

1. A method for automatically controlling by automatic control circuitry a therapeutic ultrasound transducer for ultrasonically treating tissue and comprising the steps of:
   (a) providing means for inputting tissue treatment parameters into automatic control circuitry operatively connected to a therapeutic ultrasound transducer;
   (b) upon tissue treatment parameters being entered, automatically calculating by said control circuitry an ultrasound treatment dosage based on input tissue treatment parameters said treatment dosage including at least two dosage factors which are mathematically related to said dosage;
   (c) upon no tissue treatment parameters being entered, automatically calculating by said control circuitry an ultrasound treatment dosage based on selected default tissue treatment parameters;
   (d) automatically controlling said ultrasound transducer by said control circuitry to maintain the calculated ultrasound treatment dosage;
   (e) manually varying a first of said dosage factors; and
   (f) automatically varying a second of said dosage factors to compensate for variation of the first dosage factor to thereby maintain the previously calculated dosage.

2. A method as set forth in claim 1 wherein said treatment dosage includes as dosage factors ultrasonic intensity of said transducer and a treatment time, and wherein steps (e) and (f) further include the steps of:
   (a) automatically tracking the percentage of the calculated dosage applied to said tissue;
   (b) prior to expiration of said treatment time, manually varying a first of said dosage factors; and
   (c) automatically varying a second of said dosage factors in inverse proportion to variation of said first dosage factor for a remaining percentage of the previously calculated treatment dosage to be applied to said tissue.

3. A method as set forth in claim 2 and including the steps of:
   (a) prior to expiration of said treatment time, manually varying said treatment time; and
   (b) automatically varying said ultrasound intensity in inverse proportion to variation of said treatment time for a remaining percentage of said calculated treatment dosage to be applied to said tissue.

4. A method as set forth in claim 2 and including the steps of:
   (a) prior to expiration of said treatment time, manually varying said ultrasonic intensity; and
   (b) automatically varying said treatment time in inverse proportion to variation of said ultrasonic intensity for a remaining percentage of said calculated treatment dosage to be applied to said tissue.

5. A method as set forth in claim 1 and including the step of:
   (a) manually inputting as a tissue treatment parameter a selection of an ultrasonic couplant between said transducer and an external surface of a part of the body having said tissue therebelow.

6. A method as set forth in claim 1 and including the step of:
   (a) manually inputting as a tissue treatment parameter a selection of a desired tissue temperature increase of said tissue in response to application of said treatment dosage thereto.

7. A method as set forth in claim 1 and including the step of:
   (a) manually inputting as a tissue treatment parameter a selection of a tissue depth of said tissue to receive ultrasonic energy by application of said treatment dosage thereto.

8. A method as set forth in claim 1 and including the step of:
   (a) manually inputting as a tissue treatment parameter a selection of a treatment area of said tissue to receive said treatment dosage.

9. A method as set forth in claim 1 and including the step of:
   (a) providing an ultrasonic transducer having a beam nonuniformity ratio (BNR) which is not greater than 4:1.

10. A method for automatically controlling by automatic control circuitry a therapeutic ultrasound transducer for ultrasonically treating tissue and comprising the steps of:
    (a) inputting a selection of a desired tissue treatment depth to automatic control circuitry operatively connected to a therapeutic ultrasound transducer;
    (b) inputting to said control circuitry a tissue temperature increase at the selected tissue depth;
    (c) automatically calculating by said control circuitry an ultrasound treatment dosage in terms of dosage factors of an ultrasound intensity applied to said tissue over a treatment time based on the input tissue temperature increase;
    (d) energizing said transducer at a frequency corresponding to the input tissue treatment depth;
    (e) automatically maintaining an output of ultrasonic energy from said transducer at the calculated treatment dosage;
    (f) prior to expiration of said treatment time, manually varying a first of said dosage factors; and
    (g) automatically varying a second of said dosage factors to compensate for variation of the first of said dosage factors to thereby maintain the originally calculated treatment dosage.

11. A method as set forth in claim 10 and wherein steps (f) and (g) further include the steps of:
    (a) automatically tracking the percentage of the calculated dosage applied to said tissue;
    (b) prior to expiration of said treatment time, manually varying said treatment time; and
    (c) automatically varying said ultrasound intensity in inverse proportion to variation of said treatment time for a remaining percentage of said calculated treatment dosage to be applied to said tissue.

12. A method as set forth in claim 11 and including the steps of:
    (a) until a patient receiving said dosage experiences discomfort:
       (1) manually decreasing said treatment time in time increments; and (2) for each increment of decrease of said treatment time, automatically increasing said ultrasonic intensity to maintain said calculated dosage, to thereby apply a maximum intensity of ultrasonic energy to said tissue in a minimum of treatment time commensurate with the comfort of said patient.

13. A method as set forth in claim 12 and including the steps of:
   (a) upon said patient experiencing said discomfort:
      (1) manually increasing said treatment time in time increments; and
      (2) for each increment of increase of said treatment time, automatically decreasing said ultrasonic intensity to maintain said calculated dosage, to thereby return to a maximum ultrasonic intensity level which does not cause discomfort in said patient.

14. A method as set forth in claim 10 and wherein steps (f) and (g) further include the steps of:
   (a) automatically tracking the percentage of the calculated dosage applied to said tissue;
   (b) prior to expiration of said treatment time, manually varying said ultrasonic intensity; and
   (c) automatically varying said treatment time in inverse proportion to variation of said ultrasonic intensity for a remaining percentage of said calculated treatment dosage to be applied to said tissue.

15. A method as set forth in claim 10 and including the step of:
   (a) providing an ultrasonic transducer having a beam nonuniformity ratio (BNR) which is not greater than 4:1.

16. A method as set forth in claim 10 and including the steps of:
   (a) inputting as a tissue treatment parameter at least one of:
      (1) a selection of one of a plurality a treatment areas of said tissue to receive said treatment dosage;
      (2) a selection of one of a plurality of ultrasonic couplants between said transducer and an external surface of a part of the body having said tissue therebelow;
      (3) a selection of one of a plurality of types of tissue to receive said treatment dosage; and
      (4) a selection of a duty factor of an ultrasonic signal output to be output from said transducer from a range of duty factors; and
   (b) automatically calculating said treatment dosage based upon a selection within any tissue treatment parameter which has been input.

* * * * *